(12) United States Patent
Kimata et al.

(10) Patent No.: US 9,964,367 B2
(45) Date of Patent: May 8, 2018

(54) LIFETIME DIAGNOSIS COMPONENT FOR ANTICORROSIVE COATING, HEAT EXCHANGER, REFRIGERATION-AND-AIR-CONDITIONING APPARATUS

(71) Applicant: Mitsubishi Electric Corporation, Tokyo (JP)

(72) Inventors: Akinori Kimata, Tokyo (JP); Rumi Okajima, Tokyo (JP); Yasunobu Hirai, Tokyo (JP); Kazuhiro Miya, Tokyo (JP); Hironori Kuriki, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 243 days.

(21) Appl. No.: 14/898,571

(22) PCT Filed: Oct. 31, 2013

(86) PCT No.: PCT/JP2013/079483
§ 371 (c)(1),
(2) Date: Dec. 15, 2015

(87) PCT Pub. No.: WO2015/063903
PCT Pub. Date: May 7, 2015

(65) Prior Publication Data
US 2016/0131445 A1   May 12, 2016

(51) Int. Cl.
*F28F 19/00* (2006.01)
*F28F 19/06* (2006.01)
(Continued)

(52) U.S. Cl.
CPC .......... *F28F 19/06* (2013.01); *C09D 5/08* (2013.01); *C09D 5/106* (2013.01); *C23F 13/08* (2013.01);
(Continued)

(58) Field of Classification Search
CPC ........ F28F 19/06; F28F 21/084; F28F 21/085; F28F 2200/00; F28F 2265/16; C09D 5/08;
(Continued)

(56) References Cited

U.S. PATENT DOCUMENTS 3,024,183 A * 3/1962 MacEwan ............... C23F 13/08
164/112
3,053,511 A * 9/1962 Godfrey ................. B32B 15/01
165/133
(Continued)

FOREIGN PATENT DOCUMENTS

CN    1270297 A    10/2000
CN   101676667 A    3/2010
(Continued)

OTHER PUBLICATIONS

Extended European Search Report dated Apr. 3, 2017 in the corresponding EP application No. 13896643.7.
(Continued)

*Primary Examiner* — Justin Jonaitis
(74) *Attorney, Agent, or Firm* — Posz Law Group, PLC (57) ABSTRACT

A lifetime diagnosis component for anticorrosive coating includes a plate-shaped base member having an aluminum layer on a surface thereof; and a sacrificial anode layer portion formed of zinc on the base member. The surface of the base member has a base-member exposing portion where the aluminum layer is exposed.

12 Claims, 9 Drawing Sheets

(51) Int. Cl.
    C09D 5/10      (2006.01)
    C09D 5/08      (2006.01)
    F28D 21/00     (2006.01)
    F25B 47/00     (2006.01)
    C23F 13/08     (2006.01)
    F28F 21/08     (2006.01)
    F25B 13/00     (2006.01)
    F28D 1/047     (2006.01)

(52) U.S. Cl.
    CPC ............ *F25B 47/003* (2013.01); *F28D 21/00* (2013.01); *C23F 2201/00* (2013.01); *F25B 13/00* (2013.01); *F25B 2400/071* (2013.01); *F28D 1/0478* (2013.01); *F28D 2021/0061* (2013.01); *F28F 21/084* (2013.01); *F28F 21/085* (2013.01); *F28F 2200/00* (2013.01); *F28F 2265/16* (2013.01)

(58) Field of Classification Search
    CPC ...... C09D 5/106; C23F 13/08; C23F 2201/00; F25B 47/003; F25B 13/00; F25B 2400/071; F28D 21/00; F28D 1/0478; F28D 2021/0061; Y10S 165/001; F24F 11/0086; F24F 13/029; F24F 2011/0091; Y10T 137/2836
    USPC .............................................. 165/134.1, 11.1
    See application file for complete search history.

(56) References Cited

U.S. PATENT DOCUMENTS

| | | | | | |
|---|---|---|---|---|---|
| 4,150,980 | A | * | 4/1979 | Imaizumi | C22C 21/10 420/540 |
| 4,187,690 | A | * | 2/1980 | Lindahl | F25B 30/06 165/164 |
| 4,238,233 | A | * | 12/1980 | Yamada | C22C 21/00 420/541 |
| 4,317,484 | A | * | 3/1982 | Tanabe | F28F 19/004 165/134.1 |
| 4,473,110 | A | * | 9/1984 | Zawierucha | F25J 5/002 165/133 |
| 5,127,433 | A | * | 7/1992 | Argyle | G01N 17/00 116/206 |
| 5,181,536 | A | * | 1/1993 | Argyle | G01N 17/00 116/206 |
| 2002/0050343 | A1 | * | 5/2002 | Kawamoto | C23C 30/00 165/133 |
| 2007/0235170 | A1 | * | 10/2007 | Zinck | F28F 19/06 165/133 |
| 2010/0051247 | A1 | * | 3/2010 | Sogabe | B21D 53/08 165/151 |

FOREIGN PATENT DOCUMENTS

| JP | 06-194092 A | 7/1994 |
|---|---|---|
| JP | 07-052308 A | 2/1995 |
| JP | 09-310139 A | 12/1997 |
| JP | 2010-229426 A | 10/2010 |
| JP | 2011-136358 A | 7/2011 |

OTHER PUBLICATIONS

International Search Report of the International Searching Authority dated Jan. 28, 2014 for the corresponding international application No. PCT/JP2013/079483 (and English translation).

Office Action dated Jan. 23, 2017 issued in corresponding CN patent application No. 201380078288.8 (and English translation).

Office Action dated Jul. 5, 2016 issued in corresponding JP patent application No. 2015-544706 (and English translation).

Office Action dated Sep. 22, 2017 issued in corresponding CN patent application No. 201380078288.8 (and English translation).

* cited by examiner

PROGRESS OF CORROSION AT
PORTION DEVOID OF
SACRIFICIAL LAYER SPRAYING
(SCHEMATIC ILLUSTRATION)

LIFETIME DIAGNOSIS COMPONENT FOR ANTICORROSIVE COATING, HEAT EXCHANGER, REFRIGERATION-AND-AIR-CONDITIONING APPARATUS

CROSS REFERENCE TO RELATED APPLICATION

This application is a U.S. national stage application of International Application No. PCT/JP2013/079483 filed on Oct. 31, 2013, the disclosure of which is incorporated herein by reference.

TECHNICAL FIELD

The present invention relates to a lifetime diagnosis component for anticorrosive coating, a heat exchanger, and a refrigeration-and-air-conditioning apparatus.

BACKGROUND ART

Conventional heat exchangers used in refrigeration-and-air-conditioning apparatuses have employed copper pipes. However, due to high copper price these days, relatively cheaper alternative materials are required. Under the circumstances, a refrigeration-and-air-conditioning apparatus that employs an aluminum heat exchanger made of an aluminum material, instead of a copper material, has been proposed (for example, see Patent Literature 1).

Herein, when, for example, a heat exchanger installed in a refrigeration-and-air-conditioning apparatus is serving as an evaporator, air supplied to the heat exchanger is cooled, and dew condensation water is deposited on fins and heat transfer tubes (refrigerant pipes) of the heat exchanger. Because aluminum heat exchangers have lower anticorrosive capacity than copper heat exchangers, the fins and heat transfer tubes of the heat exchangers are corroded by the dew condensation water. If the heat transfer tubes corrode, a through-hole may be formed.

To suppress this situation, in the technique disclosed in Patent Literature 1, when a refrigeration-and-air-conditioning apparatus employs an aluminum heat exchanger, a sacrificial anode layer formed of zinc (Zn layer) is formed on the surface of the heat transfer tubes. By allowing the sacrificial anode layer to corrode, corrosion of the heat transfer tubes is suppressed.

CITATION LIST

Patent Literature

Patent Literature 1: Japanese Unexamined Patent Application Publication No. 6-194092 (for example, see Abstract)

SUMMARY OF INVENTION

Technical Problem

An aluminum material is cheaper than a copper material, and thus, aluminum heat exchangers are attracting attention as an alternative to conventional copper heat exchangers. However, the aluminum material has lower anticorrosive capacity than the copper material. Hence, when the aluminum material is used for heat transfer tubes of a heat exchanger, a through-hole due to corrosion may be formed in the heat transfer tubes, and refrigerant flowing thorough the heat transfer tubes flow out into the air, which may decrease the heat exchange efficiency of the heat exchanger or place a load on the environment. Hence, the heat exchanger needs to be replaced before the through-hole is formed.

To prevent the formation of a through-hole due to corrosion in the heat transfer tubes, the anticorrosive capacity life of the heat exchanger needs to be diagnosed (estimated) in advance. However, the cause and rate of progress of corrosion vary according to the environment in which the heat exchanger is installed. Furthermore, depending on the method of forming a sacrificial anode layer, the sacrificial anode layer may not be formed at a position where the sacrificial anode layer is supposed to be formed, due to manufacturing errors or other reasons. Hence, the rate of progress of corrosion varies among heat exchangers.

As has been described, the cause and rate of progress of corrosion of the heat exchangers vary according to the environment in which the heat exchangers are installed or due to manufacturing errors. Hence, there are uncertainties in diagnosing the anticorrosive capacity life. That is, there is a problem that it is difficult to accurately diagnose the anticorrosive capacity life without deteriorating convenience.

The present invention has been made to overcome the above-described problem, and an object thereof is to provide a lifetime diagnosis component for anticorrosive coating, a heat exchanger, and a refrigeration-and-air-conditioning apparatus that enable accurate diagnosis of the anticorrosive capacity life, while suppressing deterioration of convenience.

Solution to Problem

A lifetime diagnosis component for anticorrosive coating of the present invention includes a plate-shaped base member having, on a surface thereof, an aluminum layer; and a sacrificial anode layer formed of zinc on the base member, the base member having, on the surface thereof, a base-member exposing portion in which the aluminum layer is exposed

Advantageous Effects of Invention

According to the lifetime diagnosis component for anticorrosive coating of the present invention, with the above-described configuration, it is possible to accurately diagnose the anticorrosive capacity life while suppressing deterioration of convenience.

DESCRIPTION OF EMBODIMENTS

Hereinbelow, Embodiment of the present invention be described on the basis of the drawings.

Embodiment

Figure 1:
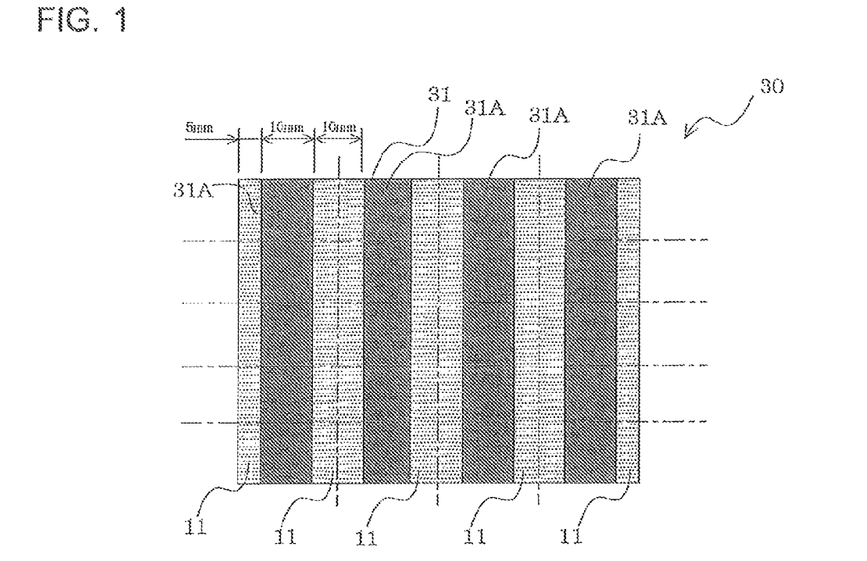
FIG. 1 is a plan view of a plate member, which has lifetime diagnosis component for anticorrosive coatings according to Embodiment of the present invention.
Figure 2:
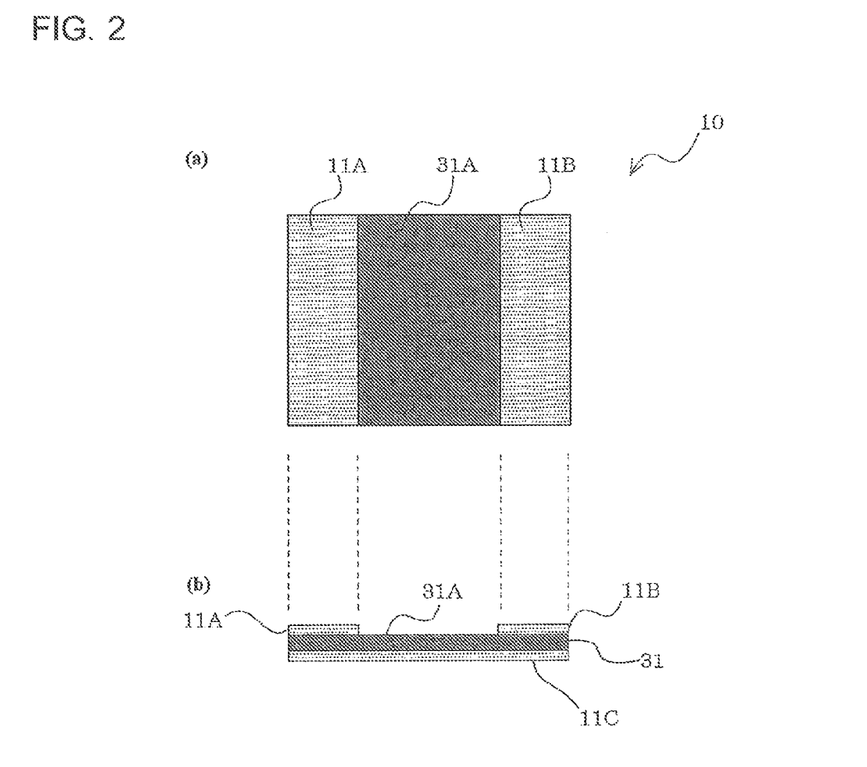
FIG. 2 is a plan view of the lifetime diagnosis component for anticorrosive coating obtained by cutting the plate member shown in FIG. 1.

FIG. 1 is a plan view of a plate member 30, which has lifetime diagnosis component 10 for anticorrosive coatings according to Embodiment. FIG. 2 is a plan view of the lifetime diagnosis component 10 for anticorrosive coating obtained by cutting the plate member 30 shown in FIG. 1. Note that FIG. 2(a) is a plan view of the lifetime diagnosis component 10 for anticorrosive coating, and FIG. 2(b) is a sectional view of the lifetime diagnosis component 10 for anticorrosive coating. In FIGS. 1 and 2(a), one side of the plate member 30 is shown.

The plate member 30 includes a plate-shaped base member 31 having an aluminum layer on the surface thereof, and sacrificial anode layer (sacrificial anode layer portions) 11 formed of zinc. Furthermore, the plate member 30 is provided with the sacrificial anode layer portions 11 that are formed by, for example, performing zinc spraying or zinc-containing-material coating on the base member 31. Note that the sacrificial anode layer portions 11 are formed at portions on one side of the plate member 30. More specifically, as shown in FIG. 1, the sacrificial anode layer portions 11 are formed at predetermined intervals on one side of the plate member 30. Hence, on one side of the plate member 30, the aluminum layer, serving as the base member 31, is exposed at portions of the base member 31 where the sacrificial anode layer portions 11 are not provided. In this manner, the sacrificial anode layer portions 11 and the portions where the aluminum layer, serving as the base member 31, is exposed (i.e., base-member exposing portions 31A, described below) are alternately arranged on the plate member 30. Although a configuration in which the base member 31 having the aluminum layer includes the lifetime diagnosis component 10 for anticorrosive coatings has been described in Embodiment, the configuration is not limited thereto, and an aluminum plate completely composed of aluminum may be used as the base member 31.

Note that a zinc layer is formed on the other side of the plate member 30. That is, as shown in FIG. 2(b), a third sacrificial anode layer 110 formed of zinc is formed on the whole surface on the other side of the plate member 30. The third sacrificial anode layer 110 forms a whole-surface sacrificial-anode layer. Note that this third sacrificial anode layer 110 is also formed by, for example, performing zinc spraying or zinc-containing-material coating. When dissimilar metals are kept in contact with each other for a long time, corrosion is accelerated at the contact surfaces of the dissimilar metals due to the electric potential difference between the metals. The lifetime diagnosis component 10 for anticorrosive coating is assumed to be mounted to a heat-exchanger sacrificial-anode layer 1A of a heat transfer tube 1 of a heat exchanger 150 (described below). Thus, the entirety of the rear surface of the lifetime diagnosis component 10 for anticorrosive coating is used as the sacrificial anode to prevent the bimetallic corrosion.

Herein, "zinc spraying" is to spray zinc on the base member 31. Hence, there is no boundary between the aluminum layer on the base member 31 and zinc. "Zinc-containing-material coating" is to apply zinc to the base member 31, and there is a boundary between the aluminum layer on the base member 31 and zinc. FIG. 2(b) shows a sectional view showing a case where zinc is applied to the base member 31 by zinc-containing-material coating. The lifetime diagnosis component 10 for anticorrosive coating according to Embodiment is attached to, for example, a heat exchanger 100 (described below) and is used to diagnose the anticorrosive capacity life of the heat exchanger 100. When diagnosing the anticorrosive capacity life, it is desirable that the condition of the lifetime diagnosis component 10 for anticorrosive coating and the condition of the heat exchanger 100 be the same. Hence, when the heat exchanger 100 is produced by zinc spraying, the lifetime diagnosis component 10 for anticorrosive coating should also be produced by zinc spraying, and when the heat exchanger 100 is produced by zinc-containing-material coating, the lifetime diagnosis component 10 for anticorrosive coating should also be produced by zinc-containing-material coating.

The lifetime diagnosis component 10 for anticorrosive coating is obtained by cutting the plate member 30, as shown in FIG. 1. That is, by cutting the plate member 30 along dashed lines shown in FIG. 1, portions of the plate member 30 delimited by the dashed lines are cut away, and the lifetime diagnosis component 10 for anticorrosive coating can be obtained.

The lifetime diagnosis component 10 for anticorrosive coating is provided with multiple strip-shaped sacrificial anode layer portions 11. Specifically, the lifetime diagnosis component 10 for anticorrosive coating is provided with a first sacrificial anode layer portion 11A formed at one end and a second sacrificial anode layer portion 11B formed at the other end. The base-member exposing portion 31A, which is a portion where the base member 31 is exposed, is provided between the first sacrificial anode layer portion 11A and the second sacrificial anode layer portion 11B. In this manner, on one side of the lifetime diagnosis component 10 for anticorrosive coating, the base-member exposing portion 31A is located between the first sacrificial anode layer portion 11A and the second sacrificial anode layer portion 11B. Note that the third sacrificial anode layer 110 including the zinc layer is formed on the entire other side of the lifetime diagnosis component 10 for anticorrosive coating. The lifetime diagnosis component 10 for anticorrosive coating is mounted to a heat transfer tube 1 such that the other surface of the base member, which is the surface with the third sacrificial anode layer 110, comes into contact with the outer surface of the heat transfer tube 1.

Figure 9:
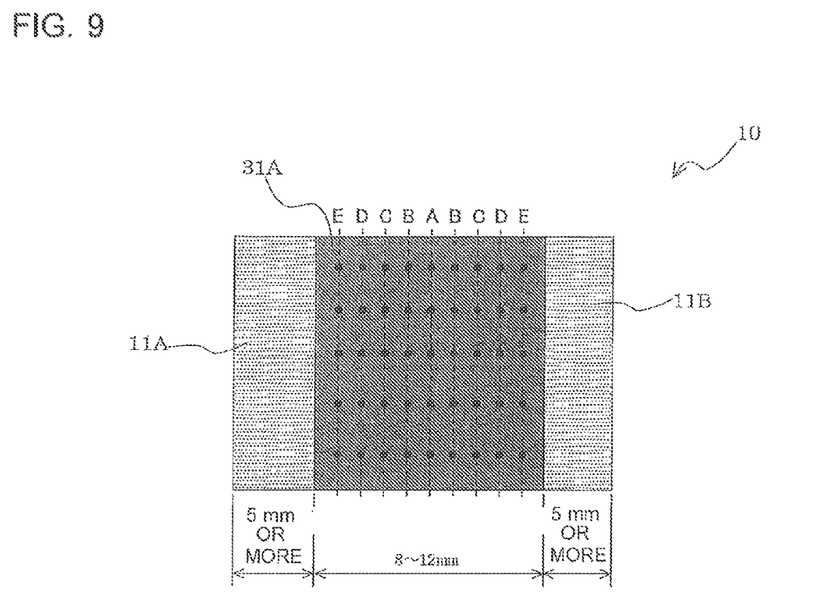
FIG. 9 is a diagram for explaining the dimensions and the like of the lifetime diagnosis component for anticorrosive coating according to Embodiment of the present invention.

The first sacrificial anode layer portion 11A and the second sacrificial anode layer portion 11B have a width, in the direction parallel to the direction from one side to the other side of the base member 31, of 5 mm or more, and the base-member exposing portion 31A has a width, in the direction parallel to the direction from one side to the other side of the base member 31, of 8 mm to 12 mm (see FIG. 9). Note that the reason why the width in the direction parallel to the direction from one side to the other side of the base member 31 is set to 8 mm to 12 mm will be described in detail in FIGS. 13 and 14 below.

Note that, although an example case where the plate member 30 includes the base member 31 having the aluminum layer and where the lifetime diagnosis component 10 for anticorrosive coating is obtained by performing zinc spraying or zinc-containing-material coating has been described in Embodiment, the configuration is not limited thereto. For example, it is also possible to use a clad plate formed by bonding an aluminum plate member and zinc plate members. That is, a clad plate formed by bonding zinc plate members, corresponding to the first sacrificial anode layer portion 11A and the second sacrificial anode layer portion 11B, with an aluminum plate member, corresponding to the base member 31, may be used. Furthermore, this clad plate may have three layers by additionally including a zinc plate member corresponding to the third sacrificial anode layer 11C. Note that, when a clad plate is used, the aluminum layer is disposed on one side of the plate member 30, so that the base-member exposing portion 31A is the aluminum layer.

Figure 3:
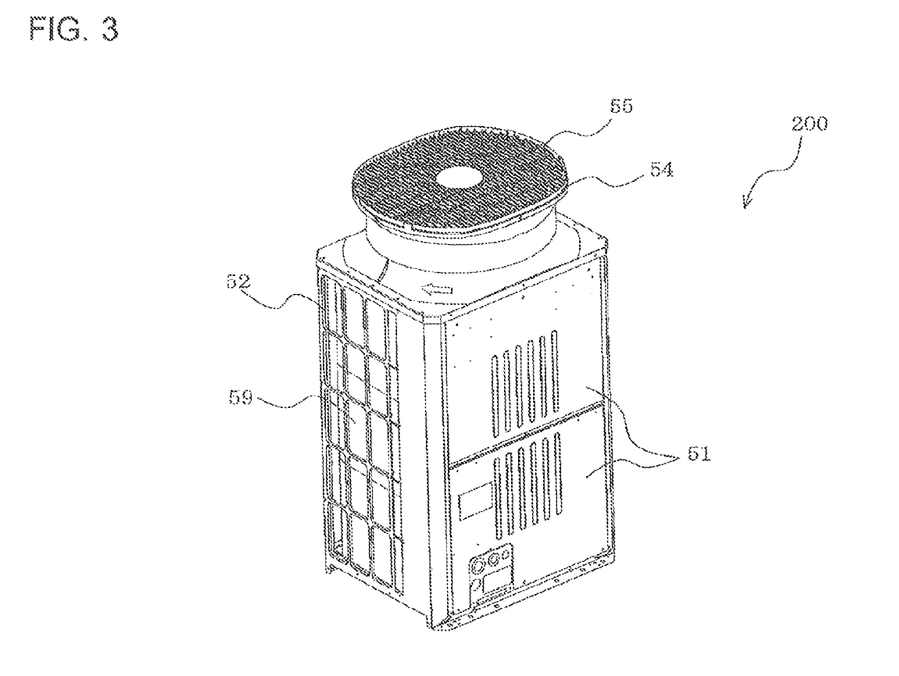
FIG. 3 is a perspective view showing the entirety of an outdoor unit, serving as a refrigeration-and-air-conditioning apparatus having the lifetime diagnosis component for anticorrosive coatings.
Figure 4:
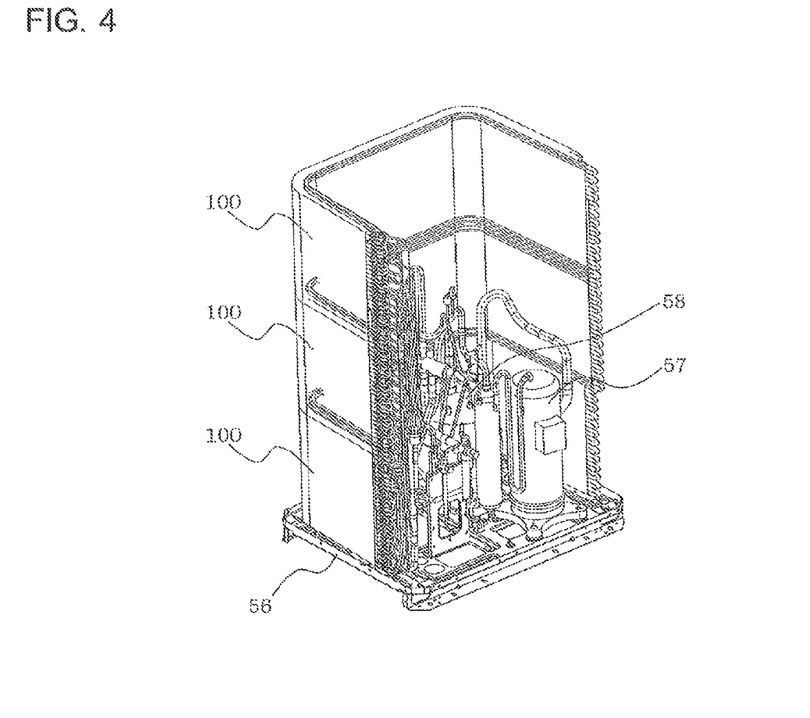
FIG. 4 is a perspective view of the outdoor unit shown in FIG. 3, in a state without a front panel, side panels, a fan, a fan guard, etc.

FIG. 3 is a perspective view showing the entirety of an outdoor unit 200, serving as a refrigeration-and-air-conditioning apparatus having the lifetime diagnosis component 10 for anticorrosive coatings. FIG. 4 is a perspective view of the outdoor unit 200 shown in FIG. 3, in a state with a front panel 51, a side panel 52, a fan, a fan guard 54, etc. having been removed. An example of the refrigeration-and-air-conditioning apparatus will be described by taking the outdoor unit 200 of the air-conditioning apparatus as an example.

The outdoor unit 200 has, for example, a vertically long housing. That is, as shown in FIG. 3, the outdoor unit 200 includes the front panel 51 that forms a housing on the front side of the outdoor unit 200, the fan guard 54 provided at the top of the outdoor unit 200, and the side panel 52 that forms the housing on the sides of the outdoor unit 200. The outdoor unit 200 is provided with air inlets 59, through which air is taken in, in the side surfaces and rear surface of the housing and is provided with an air outlet 55, through which the air is discharged outside, at the top of the outdoor unit 200. That is, the outdoor unit 200 has the air inlets 59, which are provided in the side panel 52 and used to take air into the outdoor unit 200, and the air outlet 55, which is provided in the fan guard 54 and used to discharge the air inside the outdoor unit 200 to the outside of the outdoor unit 200.

The outdoor unit 200 includes the heat exchangers 100, a base panel 56 that supports the heat exchangers 100, a compressor 57 that compresses and discharges the refrigerant, and an accumulator 58 that stores excess refrigerant.

The heat exchangers 100 cause the refrigerant supplied thereto and the air passing therethrough to exchange heat. During a cooling-mode operation, the heat exchangers 100 function as a condenser (radiator) to condense and liquefy the refrigerant, whereas during a heating-mode operation, the heat exchangers 100 function as an evaporator to evaporate and gasify the refrigerant. The heat exchangers 100 are provided at positions facing the side panel 52 and fixed to, for example, the side panel 52.

Herein, although the heat exchangers 100 are described as being vertically stacked in three layers in Embodiment, the configuration of the heat exchangers 100 is not limited thereto; a configuration in which the heat exchangers 100 are not stacked is also possible.

The base panel 56 supports the heat exchangers 100, the compressor 57, the accumulator 58, and other components, and these components are fastened to the base panel 56 with, for example, screws. The base panel 56 constitutes the housing of the outdoor unit 200 on the bottom side. The compressor 57 is disposed on, for example, the base panel 56 and compresses and discharges the refrigerant. The compressor 57 is coupled to the accumulator 58 at the suction side thereof. Furthermore, the discharge side of the compressor 57 is coupled to the heat exchangers 100 during a cooling-mode operation and is coupled to a use-side heat exchanger installed in an indoor unit (not shown) during a heating-mode operation. The accumulator 58 is coupled to the suction side of the compressor 57 and stores liquid refrigerant. Furthermore, the heat exchangers 100 are provided vertically on the rear side, right side, and left side of the accumulator 58.

Furthermore, the outdoor unit 200 is provided with a fan (not shown) used to take air into the outdoor unit 200 and to discharge the air. Note that the fan is exposed by removing the fan guard 54. The fan takes air into the outdoor unit 200 and discharges the air outside the outdoor unit 200 by rotating. The fan is provided so as to be surrounded by the fan guard 54 in this manner, and the air outlet 55 is formed above the fan. That is, the air passing through the heat exchangers 100 arranged along the air inlets 59 is drawn into the inside of the outdoor unit 200 and is discharged, through the fan, from the air outlet 55 provided in the housing, at the top.

Figure 5:
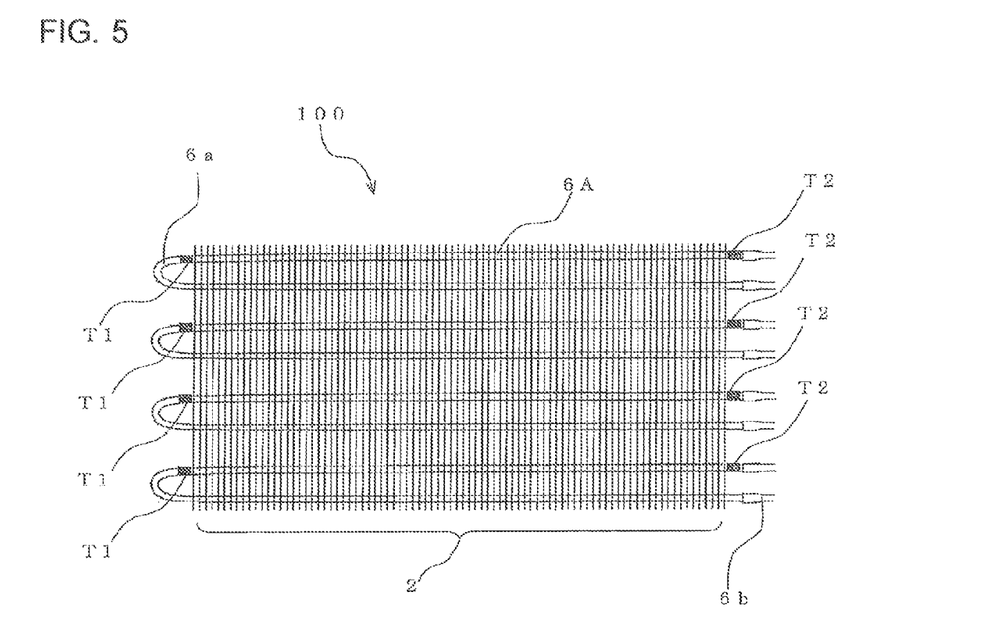
FIG. 5 is a diagram for explaining the mounting positions of the lifetime diagnosis component for anticorrosive coatings according to Embodiment of the present invention.
Figure 6:
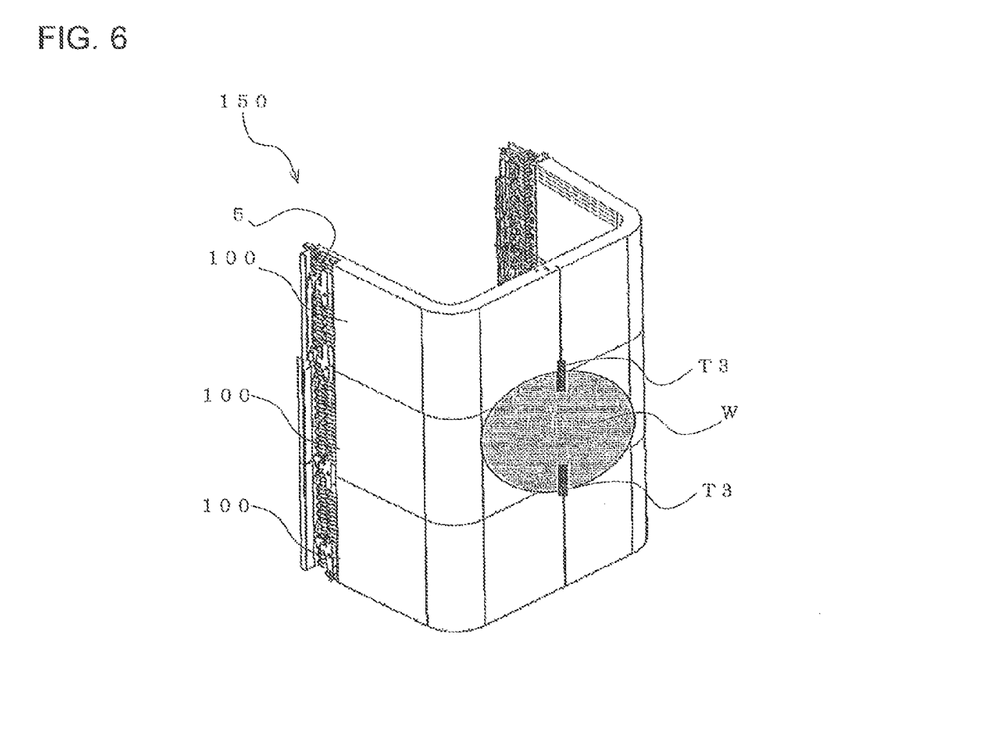
FIG. 6 is a diagram for explaining the positions, different from those in FIG. 5, where the lifetime diagnosis component for anticorrosive coatings are mounted.
Figure 7:
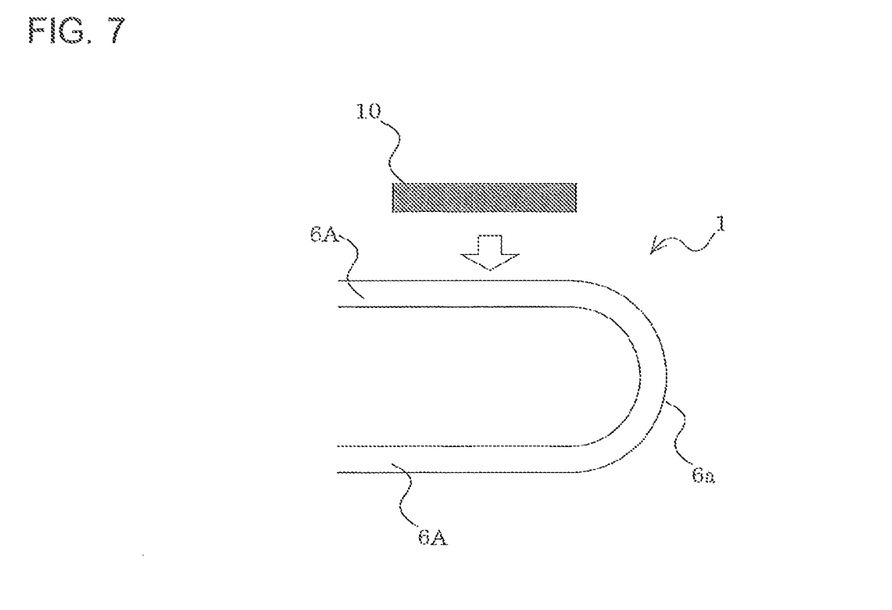
FIG. 7 is a diagram for explaining a method for mounting the lifetime diagnosis component for anticorrosive coating according to Embodiment of the present invention to a portion of a heat transfer tube, near a hairpin portion.
Figure 8:
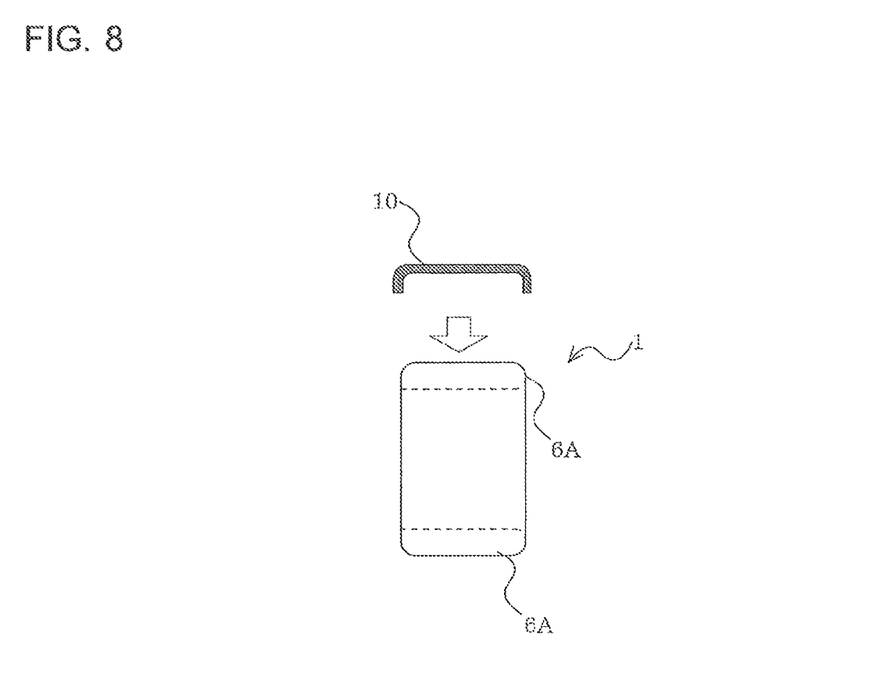
FIG. 8 is a diagram of the portion shown in FIG. 7, as viewed from the hairpin portion side, in the direction parallel to the longitudinal direction of the heat transfer tube.

FIG. 5 is a diagram for explaining the mounting positions of the lifetime diagnosis component 10 for anticorrosive coatings according to Embodiment. FIG. 6 is a diagram for explaining the positions, different from those in FIG. 5, where the lifetime diagnosis component 10 for anticorrosive coatings is mounted. FIG. 7 is a diagram for explaining a method for mounting the lifetime diagnosis component 10 for anticorrosive coating according to Embodiment to a portion of the heat transfer tube 1, near a hairpin portion 6a. FIG. 8 is a diagram of the portion shown in FIG. 7, as viewed from the hairpin portion 6a side of the heat transfer tube 1, in the direction parallel to the longitudinal direction of the heat transfer tube 1.

Note that Embodiment shows an example case where the heat exchangers 100 are flat-pipe heat exchangers, which have the flat heat transfer tubes 1. Furthermore, FIG. 6 shows a heat exchanger 150 formed by stacking the heat exchangers 100 shown in FIG. 5 in multiple layers, the heat exchangers 100 being formed by connecting the heat transfer tubes 1 to fins 2 and bent in a U shape. FIG. 6 shows an example of the heat exchanger 150 in which the heat exchangers 100 are stacked in three layers.

As shown in FIGS. 5 and 6, the heat exchangers 100 each include the heat transfer tubes 1 and the plate-shaped fins 2. The heat transfer tubes 1 each have a flow path 1*a* (see FIG. 10), through which a heat exchange medium flows. The heat transfer tube 1 includes straight portions 6A that are inserted into cutaway portions (not shown) provided in the fins 2, the U-shaped hairpin portion 6*a* continuous with the straight portions 6A and having a flat sectional shape, and aluminum joints 6*b* connected to ends of the straight portions 6A opposite from the hairpin portion 6*a*. The sectional shape of the straight portions 6A, taken in the direction perpendicular to the longitudinal direction thereof, is flat. Note that a header pipe (not shown) is connected to the aluminum joints 6*b*. Fluid, such as water, refrigerant, or brine, flows through the heat transfer tube 1. Note that, although an example case where the heat transfer tube 1 having the hairpin portion 6*a* with a flat sectional shape is used as the pipe to be inserted into the fins 2 will be described in Embodiment, the configuration is not limited thereto. For example, the heat transfer tube 1 having a bent pipe with a circular sectional shape may be used instead of the hairpin portion 6*a* with a flat sectional shape.

There are multiple fins 2 joined to the heat transfer tube 1, and therefore, the position for mounting the lifetime diagnosis component 10 for anticorrosive coating is limited. That is, if the lifetime diagnosis component 10 for anticorrosive coating is mounted to the heat exchanger 100, the fins 2 may be damaged. Hence, as shown in FIG. 5, the lifetime diagnosis component 10 for anticorrosive coating is mounted to an end of the straight portion 6A, at a position where the fins 2 are not provided, in the heat transfer tube 1. More specifically, as shown in FIG. 5, it is desirable that the lifetime diagnosis component 10 for anticorrosive coating be mounted to a portion T1, where the fins 2 are not provided, in the heat transfer tube 1; that is, a portion, in the straight portion 6A, near the hairpin portion 6*a*. More specifically, it is desirable that the lifetime diagnosis component 10 for anticorrosive coating be mounted to the straight portion 6A between the mounting position, in the straight portion 6A, of the fin 2 closest to the hairpin portion 6*a* and the position, in the straight portion 6A, where the hairpin portion 6*a* is joined.

Alternatively, as shown in FIG. 5, the lifetime diagnosis component 10 for anticorrosive coating may be mounted to a portion T2 of the heat transfer tube 1 where the fins 2 are not provided. That is, it is desirable that the lifetime diagnosis component 10 for anticorrosive coating be mounted to the portion T2, which is more distant from the hairpin portion 6*a* than the mounting position, in the straight portion 6A shown in FIG. 5, of the fin 2 farthest from the hairpin portion 6*a*. That is, it is desirable that the lifetime diagnosis component 10 for anticorrosive coating be mounted to the portion T2, in the straight portion 6A, which is close to the aluminum joint 6*b*.

When the heat exchanger installed in the refrigeration-and-air-conditioning apparatus is used in a low-temperature side, dew condensation occurs. That is, when the heat exchanger is serving as an evaporator, the water density in the air is supersaturated, and dew condenses on the heat exchanger. Because the dew condensation water deposited on the surface of the heat exchanger may accelerate corrosion, the lifetime diagnosis component 10 for anticorrosive coating needs to be placed under the same temperature environment as the heat transfer tube of heat exchanger to perform more accurate corrosion diagnosis. Hence, it is desirable that the lifetime diagnosis component 10 for anticorrosive coating be mounted so as to be in close contact with the heat transfer tube 1 of the heat exchanger 100. By making the lifetime diagnosis component 10 for anticorrosive coating in close contact with the heat exchanger 100, direct heat conduction between the heat transfer tube 1 and the lifetime diagnosis component 10 for anticorrosive coating occurs, making it possible to cause dew condensation on the heat transfer tube 1 and dew condensation on the lifetime diagnosis component 10 for anticorrosive coating at almost the same time. An example method for mounting the lifetime diagnosis component 10 for anticorrosive coating will be described below.

When the lifetime diagnosis component 10 for anticorrosive coating is mounted to the straight portion 6A, it is desirable that, as shown in FIGS. 7 and 8, the ends of the lifetime diagnosis component 10 for anticorrosive coating be bent and that the lifetime diagnosis component 10 for anticorrosive coating be mounted such that it fits the straight portion 6A. By doing so, the lifetime diagnosis component 10 for anticorrosive coating can be mounted to the straight portion 6A so as to be in close contact therewith, without using adhesive or the like. Note that the lifetime diagnosis component 10 for anticorrosive coating may be mounted to the heat transfer tube 1 by using a cord, a wire, or other means.

Herein, although a method using adhesive or other means may be an option, it should be noted that the use of adhesive may reduce the rate of heat transfer from the heat transfer tube 1 to the lifetime diagnosis component 10 for anticorrosive coating, making it difficult to establish the same condition for the lifetime diagnosis component 10 for anticorrosive coating and the heat transfer tube 1. Hence, it is preferable that, when adhesive is used, the adhesive be used within a range in which the influence of the heat conduction is not large. For example, by applying the adhesive not to the whole surface of the lifetime diagnosis component 10 for anticorrosive coating, but only to the peripheral part thereof, the influence on the heat conduction can be reduced.

Moreover, in some heat exchangers installed in the outdoor units of refrigeration-and-air-conditioning apparatuses, water is sprayed from the outside of the housing for the purpose of increasing the heat exchange efficiency. The water to be sprayed is, for example, tap water, and the tap water contains ferric ions and copper ions that have lower ionization tendencies than aluminum. Meanwhile, metal corrosion is influenced by ionization tendency. When metals having different ionization tendencies come into contact with each other, the metal having higher ionization tendency preferentially corrodes. Thus, the ferric ions and copper ions contained in tap water and deposited on the surface due to spraying water may accelerate corrosion of aluminum heat exchangers. Hence, the anticorrosive capacity life diagnosis of the heat exchanger needs to be performed at a portion where the influence of water spray is large. Accordingly, it is desirable that the lifetime diagnosis component 10 for anticorrosive coating be mounted to a portion of the heat transfer tube 1 of the heat exchanger 100 where the influence of water spray is particularly large. Note that the portion where the influence of the water spray is greatest is considered to be a water-spray area W and the vicinity thereof, where wet and dry are frequently changed.

Herein, the outdoor unit 200 according to Embodiment is also provided with a water spraying portion (not shown) at a position facing the rear surface of the heat exchanger 150. Hence, as shown in FIG. 6, it is desirable that the lifetime diagnosis component 10 for anticorrosive coating be mounted to portions T3 on the rear surface side of the heat exchanger 150. That is, it is desirable that the lifetime diagnosis component 10 for anticorrosive coating be mounted to a peripheral portion W2 of an area (water-spray area W), in the heat exchanger 150, having a certain size and subjected to water supplied from the water spraying portion. Note that the peripheral portion is a portion at the boundary between the area on which the water is sprayed and an area on which the water is not sprayed. Herein, the heat exchanger 150 is formed of the heat exchangers 100 stacked on one another. Hence, a support member (not shown) for supporting the upper and lower heat exchangers 100 may be mounted to the heat exchangers 100. Thus, the lifetime diagnosis component 10 for anticorrosive coating may be mounted to the support member such that the lifetime diagnosis component 10 for anticorrosive coating is arranged at the peripheral portion of the water-spray area W.

Furthermore, it is desirable that the thickness of the first sacrificial anode layer portion 11A and the second sacrificial anode layer portion 11B be a thickness in a predetermined range, including the thickness of the heat-exchanger sacrificial-anode layer 1A of the heat transfer tube 1. This is because it is easy to diagnose corrosion of the heat exchanger 150 when the condition of the heat exchanger 150 and the condition of the lifetime diagnosis component 10 for anticorrosive coating are the same. Hence, for example, when the thickness of the heat-exchanger sacrificial-anode layer 1A is approximately 85 μm, it is desirable that the thickness of the first sacrificial anode layer portion 11A and the second sacrificial anode layer portion 11B be set to, for example, approximately 75 μm to 100 μm.

Figure 10:
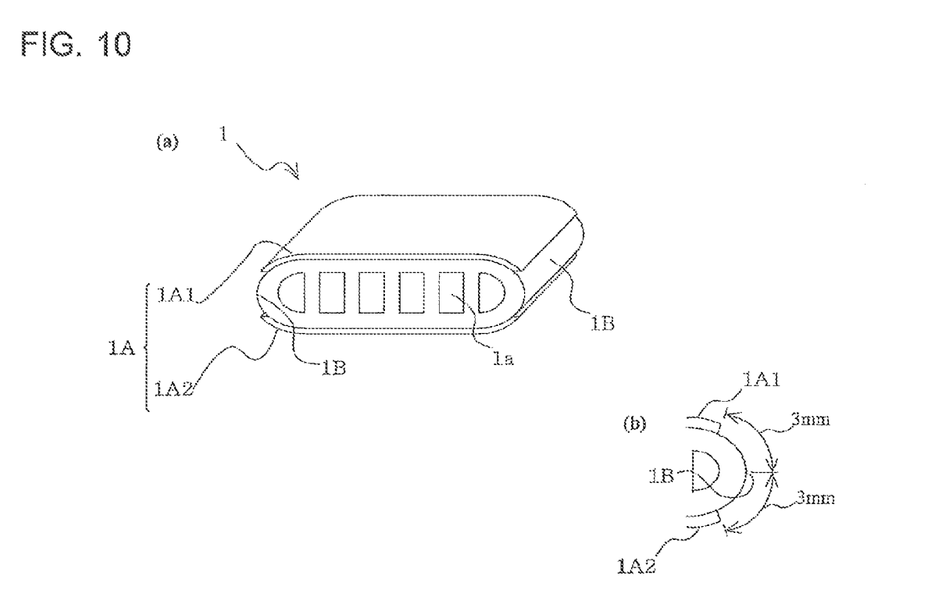
FIG. 10(a) is a vertical sectional view of the heat transfer tube of a heat exchanger.
FIG. 10(b) is a diagram showing an end of the heat transfer tube shown in FIG. 10(a).
Figure 11:
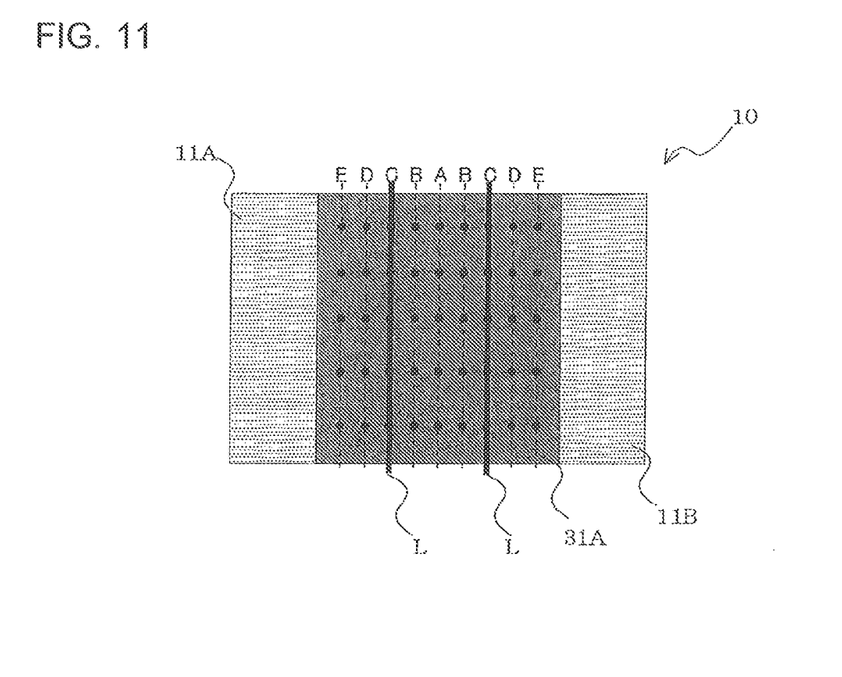
FIG. 11 is a diagram for explaining how to ascertain the anticorrosive capacity life of the heat exchanger to which the lifetime diagnosis component for anticorrosive coating is mounted.
Figure 12:
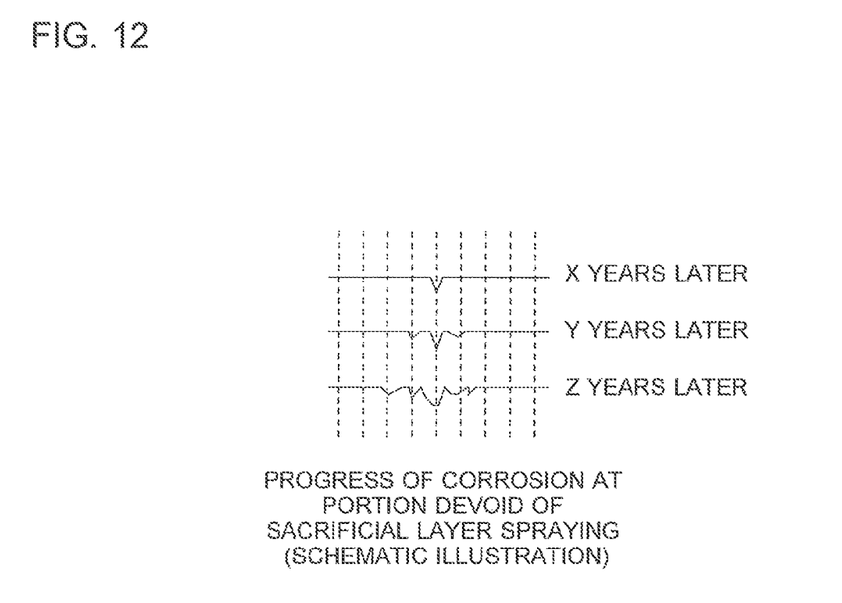
FIG. 12 shows an example corrosion state at a portion of the heat transfer tube of the heat exchanger where zinc is not sprayed.

FIG. 9 is a diagram for explaining the dimensions and the like of the lifetime diagnosis component 10 for anticorrosive coating according to Embodiment. FIG. 10(*a*) is a vertical sectional view of the heat transfer tube 1 of the heat exchanger 100, and FIG. 10(*b*) is a diagram showing an end of the heat transfer tube 1 shown in FIG. 10(*a*). FIG. 11 is a diagram for explaining how to ascertain the anticorrosive capacity life of the heat exchanger 100 to which the lifetime diagnosis component 10 for anticorrosive coating is mounted. FIG. 12 shows an example corrosion state at a portion of the heat transfer tube 1 of the heat exchanger 100 where zinc is not sprayed. Note that dashed lines A to E in FIG. 9 are used to diagnose (estimate) the time when the heat transfer tube 1 of the heat exchanger 100 to which the lifetime diagnosis component 10 for anticorrosive coating is mounted will start corroding. Furthermore, black dots on the dashed lines A to E show measuring points, where measurement as to whether corrosion has occurred is conducted.

As shown in FIG. 10, the heat transfer tube 1 of the heat exchanger 100 is provided with the heat-exchanger sacrificial-anode layer 1A formed of zinc, on the outer surface thereof. Because an aluminum material has lower anticorrosive capacity than a copper material, the heat transfer tube 1, which is an aluminum heat transfer tube, is subjected to zinc spraying, which provides sacrificial corrosion protection, on the surface of the aluminum (A3003) base member thereof to obtain improved anticorrosive capacity. The sacrificial corrosion protection is a method of protecting a more noble metal by making an electrically less noble metal selectively corrode, using the electric potential difference between the dissimilar metals. That is, in the aluminum heat exchanger, to protect the aluminum (more noble) base from corrosion, zinc (less noble) is sprayed on the aluminum surface, and zinc is made to preferentially corrode. Note that the layer of the less noble metal formed when performing sacrificial corrosion protection is called a sacrificial anode layer. Accordingly, by forming the heat-exchanger sacrificial-anode layer 1A on the heat transfer tube 1, the heat-exchanger sacrificial-anode layer 1A corrodes instead of the heat transfer tube 1. As a result, corrosion of the heat transfer tube 1 is suppressed.

As shown in FIG. 10, in a vertical sectional view of the heat transfer tube 1, the heat-exchanger sacrificial-anode layer 1A includes a first heat-exchanger sacrificial-anode layer 1A1 formed on the outer surface on one side (i.e., the upper side with respect to the sheet) and a second heat-exchanger sacrificial-anode layer 1A2 formed on the outer surface on other side (i.e., the lower side with respect to the sheet). The first heat-exchanger sacrificial-anode layer 1A1 and the second heat-exchanger sacrificial-anode layer 1A2 are formed so as to extend in the longitudinal direction of the heat transfer tube 1. The first heat-exchanger sacrificial-anode layer 1A1 and the second heat-exchanger sacrificial-anode layer 1A2 are formed on the outer surface of the heat transfer tube 1 with a predetermined distance therebetween. That is, heat-exchanger base-member-exposed portions 1B, which are portions where the heat transfer tube 1 is exposed, are provided between the first heat-exchanger sacrificial-anode layer 1A1 and the second heat-exchanger sacrificial-anode layer 1A2. In Embodiment, an example case where the width of the heat-exchanger base-member-exposed portions 1B, that is, the maximum width of the heat transfer tube 1 in the circumferential direction, is 6 mm will be described.

With the lifetime diagnosis component 10 for anticorrosive coating according to Embodiment, it is confirmed that, at positions within 5 mm from the first sacrificial anode layer portion 11A and the second sacrificial anode layer portion 11B, corrosion of the base-member exposing portion 31A is suppressed due to the effect of the sacrificial corrosion protection. That is, corrosion of the base-member exposing portion 31A starts at a position, in the base-member exposing portion 31A, far from the first sacrificial anode layer portion 11A or the second sacrificial anode layer portion 11B. Hence, corrosion of the base-member exposing portion 31A starts at the position of the line A, which is farthest from the first sacrificial anode layer portion 11A or the second sacrificial anode layer portion 11B, and an area of corrosion expands in the sequence A, B, C As the area of corrosion expands, the first sacrificial anode layer portion 11A and the second sacrificial anode layer portion 11B recede.

When the corrosion of the base-member exposing portion 31A progresses, and the corrosion of the base-member exposing portion 31A reaches corrosion start lines L, which show that the heat transfer tube 1 of the heat exchanger 100 itself starts to corrode, a serviceperson or what is in the similar role can determine that the heat transfer tube 1 itself has started to corrode. Herein, the corrosion start lines L may be any of the lines B to the lines E. For example, when the corrosion start lines L are the lines C, while the base-member exposing portion 31A corrodes at a portion between the line A and the lines C, it means that the heat transfer tube 1 itself is not corroded, but the heat-exchanger sacrificial-anode layer 1A is corroded. Then, when the corrosion of the base-member exposing portion 31A progresses beyond the lines C toward the lines D, it means that the heat transfer tube 1 itself has started to corrode.

The corrosion start lines L are determined on the basis of the effective area where the sacrificial-corrosion-protection offered by the first sacrificial anode layer portion 11A and the second sacrificial anode layer portion 11B is obtained, on the basis of the width of the heat-exchanger base-member-exposed portions 1B, or the like. When the initial maximum width (X) of the heat-exchanger base-member-exposed portions 1B of the actual device (heat exchanger 100) and the initial width of the base-member exposing portion 31A of the lifetime diagnosis component 10 for anticorrosive coating are different, the corrosion start lines L are set at positions half the width of the initial heat-exchanger base-member-exposed portions 1B (i.e., X/2) from the first sacrificial anode layer portion 11A and the second sacrificial anode layer portion 11B.

For example, when the initial maximum width (X) of the heat-exchanger base-member-exposed portions 1B assumed in the actual device is 6 mm, as shown in FIG. 10(b), the corrosion start lines L are located somewhere (i.e., the positions of the lines C here) in the area between the center of the base-member exposing portion 31A (the position of the line A) and the positions 3 mm (X/2) from the first sacrificial anode layer portion 11A and the second sacrificial anode layer portion 11B. Then, by checking the presence/absence of corrosion of the base-member exposing portion 31A on the line A and lines B, which are on the inner side of the lines C, serving as the corrosion start lines L, the degree of receding of the heat-exchanger sacrificial-anode layer 1A (the degree of progress of corrosion in the circumferential direction of the heat transfer tube 1) in the actual device (heat exchanger 100) can be known.

Note that, however, as will be described by referring to the tests and the results described in FIGS. 13 to 16 and Tables 1 to 3, the effective area of the sacrificial-corrosion-protection exists at positions 4 mm to 6 mm away from the ends of the sacrificial anode layer portions 11, and there are certain margins. Hence, for example, the degree of progress of corrosion in the circumferential direction of the heat transfer tube 1 needs to be determined, taking into consideration the possibility of an error of about ±1 mm.

Herein, the anticorrosive capacity life of the heat exchanger 100 may be represented by step 1: a first period in which the heat-exchanger sacrificial-anode layer 1A corrodes, and step 2: a second period in which the heat transfer tube 1 also corrodes. That is, the anticorrosive capacity life may be represented by step 1: the first period from when only the heat-exchanger sacrificial-anode layer 1A, instead of the heat transfer tube 1, starts to corrode to when the heat transfer tube 1 starts to corrode, and step 2: the second period from when the heat transfer tube 1 starts to corrode to when a through-hole is formed in the heat transfer tube 1.

By checking the degree of progress of corrosion by collecting the lifetime diagnosis component 10 for anticorrosive coatings at predetermined times (for example, 3 years, 5 years, 8 years, 10 years, and so on), after installation of a refrigeration-and-air-conditioning apparatus in which an actual device (heat exchanger 100) having aluminum heat transfer tubes 1 is provided with the lifetime diagnosis component 10 for anticorrosive coatings, it is possible to diagnose (estimate) the anticorrosive capacity life of the heat exchanger 100. For example, if the corrosion is observed on the line A but not on the lines B, it may be determined that the heat-exchanger sacrificial-anode layer 1A is corroded, but the heat transfer tube 1 is not yet corroded. This stage corresponds to the first period.

Moreover, because the progress of corrosion on the outer side of the lines C in FIG. 11 corresponds to the progress of corrosion of the heat-exchanger base-member-exposed portions 1B in the actual device, by checking the degree of progress of corrosion on the line A and the lines B at the time when the corrosion has started on the lines C, the rate of corrosion of the heat transfer tube 1 in the depth direction can be estimated. That is, it is considered that the more the corrosion of the base-member exposing portion 31A in the width direction (lateral direction) has progressed, the more the corrosion of base-member exposing portion 31A in the depth direction has progressed, as shown in FIG. 12. Hence, the rate per time of corrosion of the heat-exchanger base-member-exposed portions 1B of the heat transfer tube 1 in the depth direction can be estimated on the basis of the corrosion of the base-member exposing portion 31A in the lateral direction. This rate per corrosion of corrosion in the depth direction is used to calculate the second period.

In this way, the first period is estimated from the corrosion of the base-member exposing portion 31A in the width direction, and the second period is estimated from the corrosion of the base-member exposing portion 31A in the depth direction. By doing so, the anticorrosive capacity life of the heat exchanger 100 can be diagnosed.

For example, if the corrosion of the base-member exposing portion 31A has reached the lines B, serving as the corrosion start lines L, the first period, which is the time for the corrosion to reach the lines C, can be calculated on the basis of the rate per time of corrosion, at which the corrosion progresses from the line A to the lines B. Furthermore, by estimating the rate of corrosion of the heat-exchanger base-member-exposed portions 1B in the depth direction on the basis of the time taken from the line A to the lines B, it can be determined when a through-hole is likely to be formed in the heat transfer tube 1 because the thickness of the heat transfer tube 1 is known, and the second period can be calculated. The anticorrosive capacity life of the heat exchanger 100 can be calculated by adding the calculated first period and second period together. In this way, the anticorrosive capacity life of the heat transfer tube 1 can be accurately calculated by mounting the lifetime diagnosis component 10 for anticorrosive coatings, checking to which lines the corrosion has reached, and performing predetermined calculations.

Needless to say, the corrosion of the base-member exposing portion 31A in the depth direction may be actually measured to estimate the rate of corrosion of the heat-exchanger base-member-exposed portions 1B of the heat transfer tube 1 in the depth direction on the basis of the results of measurement.

Furthermore, in Embodiment, a case where the initial maximum width (X) of the heat-exchanger base-member-exposed portions 1B is 6 mm, as described above, has been assumed and described. Herein, when the heat exchanger 100 is produced by zinc spraying, it is difficult to spray zinc on the left and right ends of the heat transfer tube 1 shown in FIG. 10. That is, due to manufacturing errors or other reasons, zinc may not be sprayed on the corresponding positions of the heat-exchanger base-member-exposed portions 1B. Hence, in Embodiment, the worst case where zinc is not sprayed on the left and right ends of the heat transfer tube 1, as shown in FIG. 10, is assumed, and the heat-exchanger base-member-exposed portions 1B have been described as having a width of 6 mm.

Hence, if zinc spraying is appropriately performed, the width of the heat-exchanger base-member-exposed portions 1B may be 2 mm. In such a case, the corrosion start lines L are located somewhere (i.e., the positions of the lines E here) in the area between the center of the base-member exposing portion 31A (the position of line A) and the positions at distance of 1 mm (X/2) from each of the first sacrificial anode layer portion 11A and the second sacrificial anode layer portion 11B.

Furthermore, although the width of the base-member exposing portion 31A is set in the range of 8 mm to 12 mm in Embodiment, even when the width of the base-member exposing portion 31A exceeds 12 mm, the area protected from corrosion, extending from the edges of the first sacrificial anode layer portion 11A and the second sacrificial anode layer portion 11B, does not change and remains 4 mm to 6 mm. Accordingly, the corrosion protection effect offered by the first sacrificial anode layer portion 11A and the second sacrificial anode layer portion 11B cannot be obtained at a portion, of the base-member exposing portion 31A, at least 6 mm away from each of the first sacrificial anode layer portion 11A and the second sacrificial anode layer portion 11B. In such a portion where the corrosion protection effect cannot be obtained, corrosion occurs in the same way as on the line A described above. That is, the portion where the corrosion protection effect cannot be obtained is treated in the same way as the line A. Even in the case like this where the width of the base-member exposing portion 31A exceeds 12 mm, the lifetime diagnosis component 10 for anticorrosive coatings may be used in the same way as those with the base-member exposing portion 31A having a width of 8 mm to 12 mm.

Tests on Effective Area of Sacrificial-Corrosion-Protection and the Like

Figure 13:
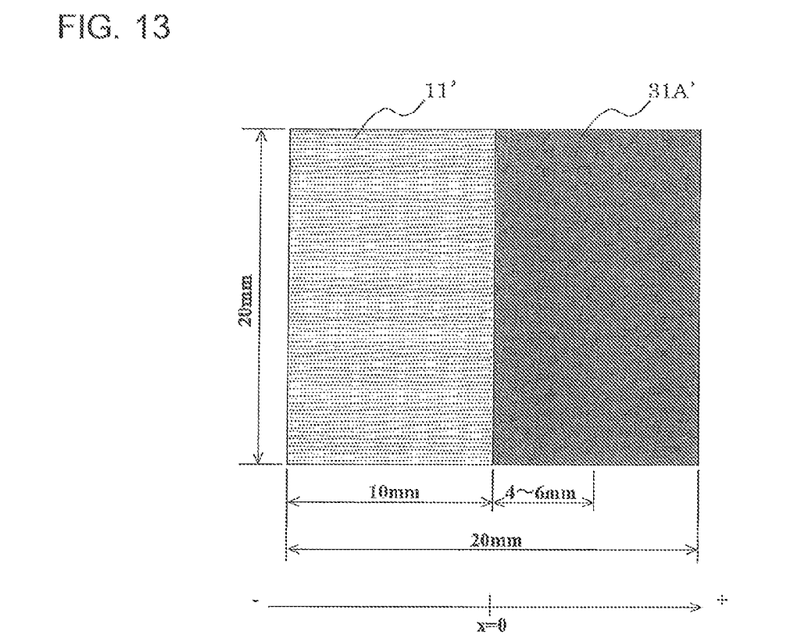
FIG. 13 is a diagram for explaining a sample used in a test for finding an effective area of the sacrificial corrosion protection.
Figure 14:
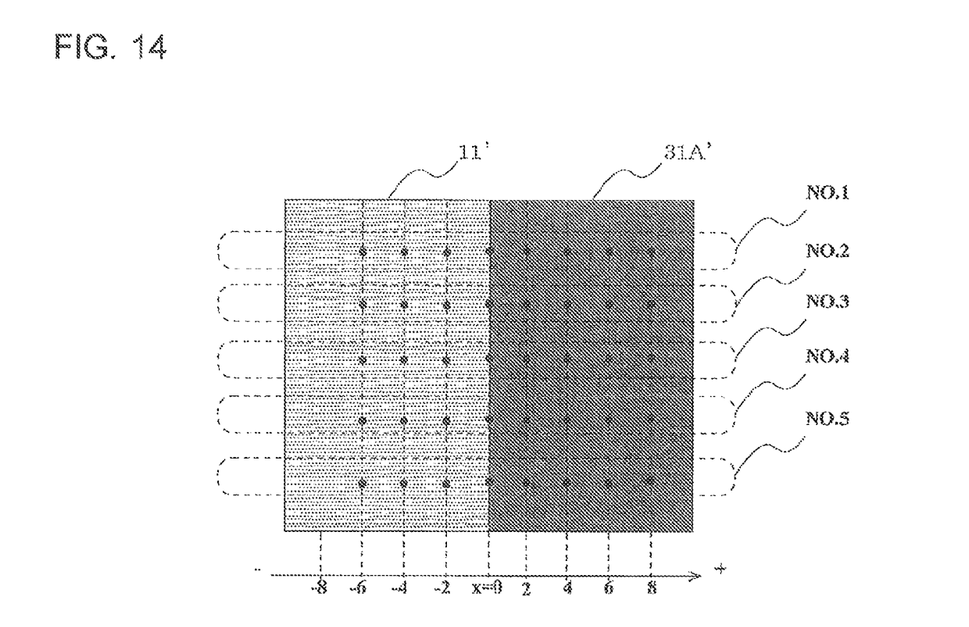
FIG. 14 is a diagram showing corrosion-depth measurement points in the sample shown in FIG. 13.
Figure 15:
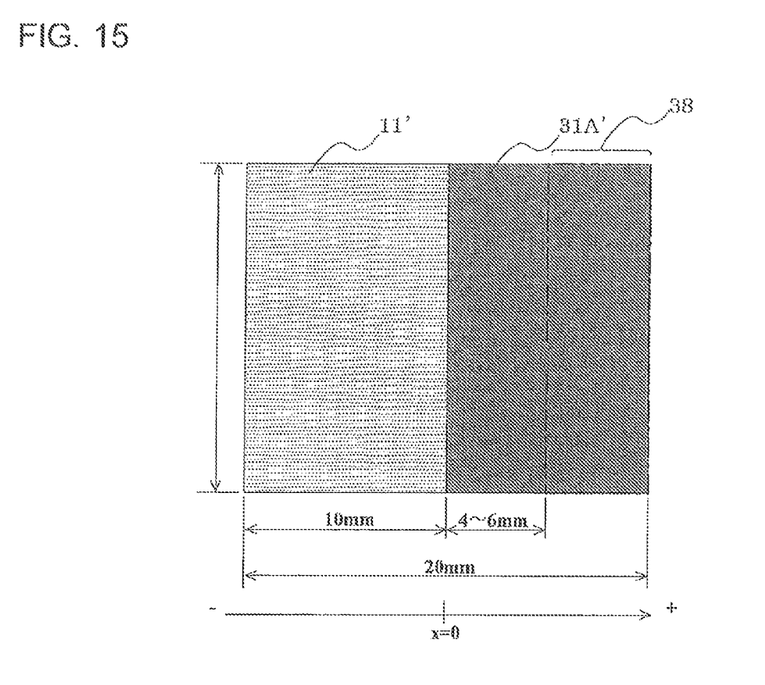
FIG. 15 is a diagram for explaining the effective area of the sacrificial anode layer.
Figure 16:
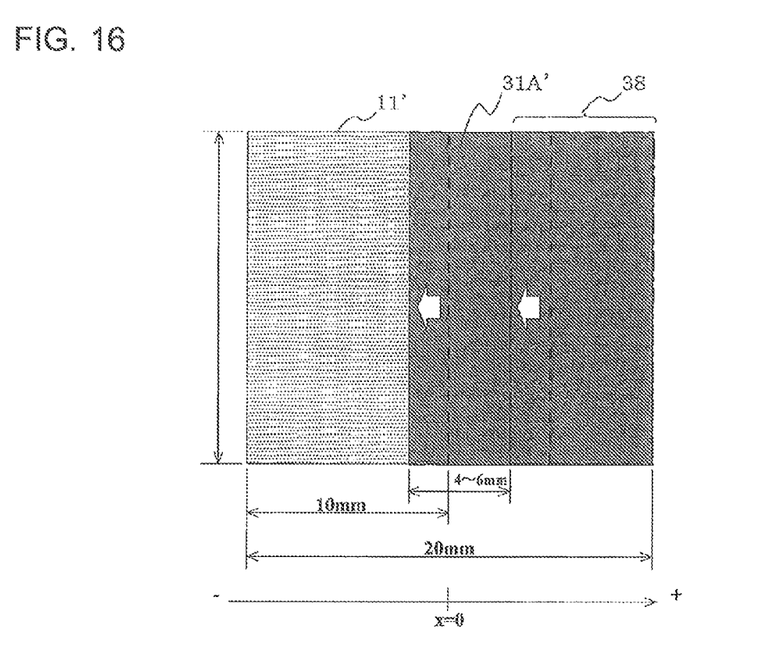
FIG. 16 is a diagram showing the sacrificial-anode-layer receded due to corrosion.

FIG. 13 is a diagram for explaining a sample used in a test for finding an effective area of the sacrificial corrosion protection. FIG. 14 is a diagram showing corrosion-depth measurement points in the sample shown in FIG. 13. FIG. 15 is a diagram for explaining the effective area of a sacrificial anode layer portion 11'. FIG. 16 is a diagram showing the sacrificial anode layer portion 11' receded due to corrosion. Referring to FIGS. 13 to 16, the test performed on the sample according to the lifetime diagnosis component 10 for anticorrosive coating and the results will be described.

As shown in FIG. 13, a sample for corrosion acceleration test, which was an aluminum plate having a size of 20 mm×20 mm with a sacrificial anode (sprayed zinc) layer having a size of 10 mm×20 mm formed to a thickness of 75 μm to 100 μm on the left half thereof, was prepared. Note that the coordinates were defined by assuming the interface between a base-member exposing portion 31A' and the sacrificial anode layer portion 11' to be x=0, the base-member exposing portion 31A' side to be positive, and the sacrificial anode layer portion 11' side to be negative.

Furthermore, as shown in FIG. 14, at each of the coordinates with x=−8, −6, −4, −2, 0, 2, 4, 6, and 8, points No. 1 to No. 5 were defined at equal intervals in the vertical direction, and these points were used as the corrosion-depth measurement points.

A corrosion acceleration test with n=5 was performed on the sample shown in FIG. 13 according to the combined cyclic corrosion test shown in Table 1.

TABLE 1

| METHOD OF TEST | | CONDITIONS OF TEST |
|---|---|---|
| 1. SPRAY | TEMPERATURE | 35 ± 1 degree(s) Celsius |
| | SPRAY | Corrosive Liquid (chloride ion |

TABLE 1-continued

| METHOD OF TEST | | CONDITIONS OF TEST |
|---|---|---|
| | LIQUID | concentration: equivalent to 5% NaCl SOLUTION, pH = 7) |
| 2. DRY | TEMPERATURE | 60 ± 1 degree(s) Celsius |
| | RELATIVE HUMIDITY | 20-30% RH |
| 3. WET | HUMIDITY | 50 ± 1 degree(s) Celsius |
| | RELATIVE HUMIDITY | 95% RH or more |
| 4. TIME AND CONTENT PER CYCLE | | SPRAY: 2 h, DRY: 4 h, WET: 2 h |

After 480 hours, the section of the sample for corrosion acceleration test was observed. The results of measurement of the depth of corrosion in the base member are shown in Table 2. In No. 1, the base member corroded by 2 mm at x=6 mm and by 5 mm at x=8 mm. In No. 2, the base member corroded by 4 mm at x=8 mm. In No. 3, the base member corroded by 1 mm at x=6 mm and by 6 mm at x=8 mm. In No. 4, the base member corroded by 6 mm at x=8 mm. In No. 5, the base member corroded by 7 mm at x=8 mm.

From above, the base member did not corrode at all in x=−8 mm to 4 mm. Furthermore, at x=6 mm, the corrosion of the base member had progressed in No. 1 and No. 3. That is, from the fact that the corrosion of the base member had not progressed at positions within 4 mm to 6 mm from the interface with respect to the sacrificial anode layer portion 11' of the sample, it is thought that, as shown in FIG. 15, sacrificial corrosion protection is effective within 4 mm to 6 mm from the edge of the sacrificial anode layer portion 11'.

TABLE 2

| | x[mm] | | | | | | | | |
|---|---|---|---|---|---|---|---|---|---|
| No. | −8 | −6 | −4 | −2 | 0 | 2 | 4 | 6 | 8 |
| 1 | 0 | 0 | 0 | 0 | 0 | 0 | 0 | 2 | 5 |
| 2 | 0 | 0 | 0 | 0 | 0 | 0 | 0 | 0 | 4 |
| 3 | 0 | 0 | 0 | 0 | 0 | 0 | 0 | 1 | 6 |
| 4 | 0 | 0 | 0 | 0 | 0 | 0 | 0 | 0 | 6 |
| 5 | 0 | 0 | 0 | 0 | 0 | 0 | 0 | 0 | 7 |

The sample shown in FIG. 13 was further subjected to the corrosion acceleration test, and the depth of corrosion was measured by observing the section in 960 hours and in 2160 hours. The presence/absence of an uncorroded part of the sacrificial anode layer portion 11' and the depth of corrosion in the base member 31' at the respective measuring points are shown in Table 3. Note that the presence/absence of the uncorroded part of the sacrificial anode layer portion 11' was determined by observing the section with SEM-EDX. Herein, SEM refers to a scanning electron microscope, and EDX refers to energy dispersive X-ray analysis. By checking the presence/absence of the uncorroded part of the sacrificial anode layer portion 11' (zinc layer) at the respective measuring points with the SEM-EDX, the depth of corrosion was determined. Herein, in Table 3, a mark "o" represents the presence of the uncorroded part of the sacrificial anode layer portion 11', a mark "x" represents the absence of the uncorroded part of the sacrificial anode layer portion 11', and a mark "-" represents the absence of the uncorroded part of the sacrificial anode layer portion 11' from the beginning. Furthermore, the depth of corrosion in the base member at each coordinate is the average of No. 1 to No. 5.

In 480 hours, there was the uncorroded part of the sacrificial anode layer portion 11' at x=0 mm. At x=6 mm, the base member corroded by 1 mm.

In 960 hours, there was the uncorroded part of the sacrificial anode layer portion 11' at x=−4 mm. At x=2 mm, the base member corroded by 4 mm.

In 2160 h, there was the uncorroded part of the sacrificial anode layer portion 11' at x=−8 mm. At x=−2 mm, the base member corroded by 3 mm.

From above, it is considered that the corrosion progresses so as to maintain a distance of at least 4 mm to 6 mm between the edge of the sacrificial anode layer portion 11' and the corrosion in the base member. That is, as shown in FIG. 16, it is considered that the interface between the sacrificial anode layer portion 11' and the base-member exposing portion 31A' receded to the left with the progress of corrosion, and a corrosion progress area 38 of the base-member exposing portion 31A' expanded by the same distance as the distance by which the interface has receded.

the corrosion protection effect offered by the sacrificial anode layer 91 cannot be obtained at a portion, of the base-member exposing portion 92, at least 6 mm away from the sacrificial anode layer 91. In such a portion where the corrosion protection effect cannot be obtained, corrosion occurs in the same way as on the line A described above. That is, the portion where the corrosion protection effect cannot be obtained is treated in the same way as the line A. Even in the case like this where the width of the base-member exposing portion 92 exceeds 6 mm, the lifetime diagnosis component for anticorrosive coatings 90 may be used in the same way as those with the base-member exposing portion 92 having a width of less than or equal to 6 mm.

Although, as a method of manufacturing the lifetime diagnosis component 10 for anticorrosive coating, the method in which the plate member 30 as shown in FIG. 1 is formed and then cut along the dashed lines shown in FIG. 1 has been described, the method is not limited thereto. That is, as long as the sacrificial anode layer portions 11, the base-member exposing portion 31A, the sacrificial anode layer 91, and the base-member exposing portion 92 having predetermined dimensions can be obtained, as in the lifetime diagnosis component 10 for anticorrosive coating shown in FIG. 9 and the lifetime diagnosis component for anticorrosive coating 90 shown in FIG. 17, the method is not limited to a method in which the plate member 30 as shown in FIG. 1 is formed and cut.

TABLE 3

| TEST TIME [h] | | x [mm] | | | | | | | | |
|---|---|---|---|---|---|---|---|---|---|---|
| | | −8 | −6 | −4 | −2 | 0 | 2 | 4 | 6 | 8 |
| 480 | PRESENCE/ABSENCE OF SACRIFICIAL-ANODE LAYER | o | o | o | o | o | — | — | — | — |
| | DEPTH OF CORROSION IN BASE MEMBER | 0 | 0 | 0 | 0 | 0 | 0 | 0 | 1 | 6 |
| 960 | PRESENCE/ABSENCE OF SACRIFICIAL-ANODE LAYER | o | o | o | x | x | — | — | — | — |
| | DEPTH OF CORROSION IN BASE MEMBER | 0 | 0 | 0 | 0 | 0 | 4 | 8 | 16 | 20 |
| 2160 | PRESENCE/ABSENCE OF SACRIFICIAL-ANODE LAYER | o | x | x | x | x | — | — | — | — |
| | DEPTH OF CORROSION IN BASE MEMBER | 0 | 0 | 0 | 3 | 7 | 11 | 18 | 30 | 43 |

UNIT: mm
o: PRESENCE OF UNCORRODED PART OF SACRIFICIAL-ANODE LAYER
x: ABSENCE OF UNCORRODED PART OF SACRIFICAL ANODE LAYER
—: ABSENCE OF SACRIFICIAL-ANODE LAYER FROM BEGINNING

Modification

Figure 17:
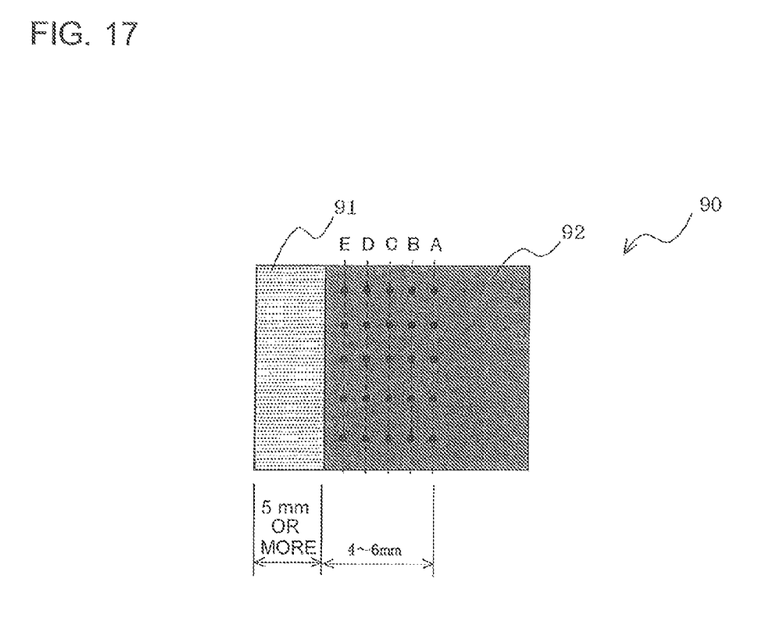
FIG. 17 shows a modification of the lifetime diagnosis component for anticorrosive coating according to Embodiment of the present invention.

FIG. 17 shows a modification (lifetime diagnosis component for anticorrosive coating 90) of the lifetime diagnosis component 10 for anticorrosive coating according to Embodiment. Although an example of the lifetime diagnosis component 10 for anticorrosive coating in which the sacrificial anode layer portions 11 are formed on both sides of the base-member exposing portion 31A has been described, a configuration in which a sacrificial anode layer 91 is formed on one side, as shown in FIG. 17, also provides the same advantage as that achieved by the lifetime diagnosis component 10 for anticorrosive coating. That is, similarly to the sacrificial anode layer portions 11 of the lifetime diagnosis component 10 for anticorrosive coating, the distance, from the edge surface of the sacrificial anode layer 91, over which corrosion is prevented does not change and remains 4 mm to 6 mm. Accordingly, although the number of the corrosion-depth measurement points is reduced to half, the lifetime diagnosis component for anticorrosive coating 90 with the sacrificial anode layer 91 formed only on one side of the base-member exposing portion 92 may also be used to diagnose the anticorrosive capacity life.

Furthermore, even if the width of the base-member exposing portion 92 exceeds 6 mm, the area, from the edge of the sacrificial anode layer 91, in which corrosion is prevented does not change and remains 4 mm to 6 mm. Accordingly,

Advantages of Embodiment

The lifetime diagnosis component 10 for anticorrosive coating according to Embodiment enables accurate calculation of the anticorrosive capacity life of the heat transfer tube 1 by mounting the lifetime diagnosis component 10 for anticorrosive coating to the heat exchanger 100, checking to which lines the corrosion has reached, and performing predetermined calculations.

Furthermore, the lifetime diagnosis component 10 for anticorrosive coating according to Embodiment can be easily mounted to a predetermined portion of the heat exchanger 100, taking into consideration the fact that the cause and rate of progress of corrosion of the heat exchanger 100 vary according to the environment in which the heat exchanger 100 is installed. For example, the lifetime diagnosis component 10 for anticorrosive coating is a compact plate-shaped member, and hence, it may be mounted either to the peripheral portion (portions T3) of the area (water-spray area W) having a certain size and subjected to water spraying supplied from the water spraying portion or to the portion (portion T1 or portion T2), of the heat transfer tube 1, where the fins 2 are not disposed. Hence, even when there are uncertainties in diagnosing the anticorrosive capacity life, it is possible to accurately diagnose the anticorrosive capacity life, while suppressing deterioration of convenience.

Because the lifetime diagnosis component 10 for anticorrosive coating according to Embodiment enables accurate diagnosis of anticorrosive capacity life, a serviceperson or other persons can determine appropriate maintenance timing for the heat exchanger 100 and the refrigeration-and-air-conditioning apparatus having the heat exchanger 100. Thus, it is possible to prevent the heat exchanger 100 and the refrigeration-and-air-conditioning apparatus having the heat exchanger 100 from becoming defective due to corrosion, when brought to market.

REFERENCE SIGNS LIST 1 heat transfer tube, 1A heat-exchanger sacrificial-anode layer, 1A1 first heat-exchanger sacrificial-anode layer, 1A2 second heat-exchanger sacrificial-anode layer, 1B heat-exchanger base-member-exposed portion, 1a flow path, 2 fin, 6A straight portion, 6a hairpin portion, 6b aluminum joint, 10 lifetime diagnosis component for anticorrosive coating, 11 sacrificial anode layer, 11A first sacrificial anode layer, 11B second sacrificial anode layer, 110 third sacrificial anode layer, 30 plate member, 31 base member, 31A base-member exposing portion, 38 corrosion progress area, 51 front panel, 52 side panel, 54 fan guard, 55 air outlet, 56 base panel, 57 compressor, 58 accumulator, 59 air inlet, 90 lifetime diagnosis component for anticorrosive coating, 91 sacrificial anode layer, 92 base-member exposing portion, 100 heat exchanger, 150 heat exchanger, 200 outdoor unit. L corrosion start line, T1 portion, T2 portion, T3 portion, and W water-spray area.

The invention claimed is:

1. A lifetime diagnosis component for anticorrosive coating, comprising:
    a plate-shaped base member,
    an aluminum layer on one surface of the plate-shaped member,
    a plurality of sacrificial anode layer portions comprising zinc provided on a surface of the aluminum layer, the plurality of sacrificial anode layer portions each being strip-shaped and spaced at intervals along the surface of the aluminum layer, and
    the surface of the aluminum layer uncoated by the plurality of sacrificial anode layer portions is exposed for diagnosis.

2. The lifetime diagnosis component for anticorrosive coating according to claim 1, wherein the exposed portion of the aluminum layer has a width of 8 mm to 12 mm.

3. The lifetime diagnosis component for anticorrosive coating according to claim 1, wherein each of the sacrificial anode layer portions has a width of 5 mm or more.

4. The lifetime diagnosis component for anticorrosive coating according to claim 1, wherein one side of the base member is provided with the plurality of sacrificial anode layer portions and the exposed portion of the aluminum layer on one side and a whole-surface sacrificial-anode layer of zinc is provided on a whole surface of another side of the base member.

5. The lifetime diagnosis component for anticorrosive coating according to claim 1, wherein the plurality of sacrificial anode layer portions are formed of a clad plate bonded to the base member.

6. The lifetime diagnosis component for anticorrosive coating according to claim 1, wherein the plurality of sacrificial anode layer portions are formed by zinc spraying or zinc-containing-material coating.

7. A heat exchanger comprising:
    the lifetime diagnosis component for anticorrosive coating according to claim 1;
    a plurality of flat-plate-shaped fins; and
    a heat transfer tube composed of aluminum, the heat transfer tube having straight portions to be attached to the fins and a hairpin portion that is bent and connected to the straight portions at ends thereof,
    wherein a heat-exchanger sacrificial-anode layer formed of zinc is formed on an outer surface of the heat transfer tube.

8. The heat exchanger according to claim 7, wherein the plurality of sacrificial anode layer portions of the lifetime diagnosis component for anticorrosive coating has a thickness within a predetermined range, including a thickness of the heat-exchanger sacrificial-anode layer of the heat transfer tube.

9. The heat exchanger according to claim 7, wherein the lifetime diagnosis component for anticorrosive coating is mounted to an end side of the straight portion of the heat transfer tube and at a position where the fins are not provided.

10. The heat exchanger according to claim 7, wherein the lifetime diagnosis component for anticorrosive coating is mounted to the heat transfer tube, wherein another surface of the base member and an outer surface of the heat transfer tube are in contact with each other.

11. A refrigeration-and-air-conditioning apparatus comprising the heat exchanger according to claim 7.

12. The refrigeration-and-air-conditioning apparatus according to claim 11, wherein the lifetime diagnosis component for anticorrosive coating is mounted to portion of a water spray an area in the heat exchanger where water is sprayed.

* * * * *